United States Patent [19]

Glidewell et al.

[11] Patent Number: 5,426,971

[45] Date of Patent: Jun. 27, 1995

[54] ON-BOARD DETECTION OF FUEL LINE VAPOR

[75] Inventors: John M. Glidewell, Dearborn; Granger K.-C. Chui, Dearborn Heights; Woong-Chul Yang, Ann Arbor, all of Mich.

[73] Assignee: Ford Motor Company, Dearborn, Mich.

[21] Appl. No.: 206,683

[22] Filed: Mar. 3, 1994

[51] Int. Cl.[6] .............................................. G01N 7/14
[52] U.S. Cl. ................................ 73/19.05; 73/19.03; 123/516; 123/518
[58] Field of Search ................. 73/19.01, 19.03, 19.05; 123/516, 518; 340/438, 451

[56] References Cited

U.S. PATENT DOCUMENTS

| | | | |
|---|---|---|---|
| 3,789,819 | 2/1974 | Moulds | 123/516 |
| 4,079,717 | 3/1978 | Shirose | 123/516 |
| 4,211,119 | 7/1980 | Wolber | 73/721 |
| 4,257,260 | 3/1981 | Beatson . | |
| 4,261,209 | 4/1981 | Hatsuno et al. | 73/753 |
| 4,732,131 | 3/1988 | Hensel | 123/516 |
| 4,791,810 | 12/1988 | Old et al. . | |
| 4,878,474 | 11/1989 | Hack, Jr. | 123/516 |
| 4,930,482 | 6/1990 | Kako | 123/488 |
| 4,977,872 | 12/1990 | Hartopp . | |
| 5,020,362 | 6/1991 | Hart et al. . | |
| 5,137,002 | 8/1992 | Mahoney et al. | 123/516 |
| 5,216,991 | 6/1993 | Iida et al. | 123/518 |
| 5,251,482 | 10/1993 | Bates et al. | 73/290 |

FOREIGN PATENT DOCUMENTS

| | | |
|---|---|---|
| 57-20553 | 2/1982 | Japan . |
| 588263 | 1/1983 | Japan . |
| 143383 | 6/1988 | Japan . |
| 150463 | 6/1988 | Japan . |
| 1389408 | 3/1975 | United Kingdom . |

OTHER PUBLICATIONS

Yang et al.; *Dynamic Modeling and Analysis of Automotive Multi-Port elec. Fuel Delivery System;* Mar. 1991; 143-151.

*Primary Examiner*—Richard E. Chilcot, Jr.
*Assistant Examiner*—Eric S. McCall
*Attorney, Agent, or Firm*—Peter Abolins; Roger L. May

[57] ABSTRACT

An on-board diagnostic system is provided for determining the presence of vapor in a fuel supply line of an internal combustion engine during engine operation. Sensing means are operatively mounted to the fuel supply line for sensing transient fuel pressure waves resulting from actuation of one or more fuel injectors. The sensing means generates a pressure signal corresponding to the transient fuel pressure waves at least over a selected test interval. Signal processing means receives the pressure signal and determines its resonance frequency over at least a selected frequency range. The test interval resonance frequency is compared to a stored resonance frequency corresponding to an acceptable vapor level in the fuel supply line. The signal processing means generates an output signal upon detecting a value difference greater than a preselected amount (e.g., greater than zero) between the test interval resonance frequency and the stored resonance frequency. Utilization means are provided for response to the output signal, for example, by illumination of an indicator light visible to the operator of a motor vehicle in which the engine is equipped with the on-board diagnostic system of the invention.

11 Claims, 4 Drawing Sheets

ON-BOARD DETECTION OF FUEL LINE VAPOR

INTRODUCTION

The present invention is directed to a diagnostic system for an internal combustion engine to detect vapor, particularly fuel vapor, in a fuel rail or other fuel supply line to the engine. More specifically, the invention is directed to an on-board diagnostic system for detecting such fuel line vapor during engine operation.

BACKGROUND OF THE INVENTION

It is becoming increasingly desirable to provide on-board diagnostic means for certain components of internal combustion engines, especially components which have a major impact on critical engine performance criteria. This is particularly true in the motor vehicle industry, where high precision in the control of fuel supply to the engine has become essential to various present and planned engine management features designed to meet increasingly strict emissions, performance, drivability, and maintenance objectives. It is now well known how to adjust the fuel flow to the cylinders of an engine to maintain desired fuel/air mixture ratio for meeting engine emission requirements by electronically controlling the actuation timing and duration of the engine's fuel injectors. Electronic fuel injector control may be incorporated into known electronic engine control (EEC) modules performing a variety of engine control functions. In accordance with such known systems, the timing of injector actuation is controlled by the timing of the corresponding actuation signal sent by the control module. The duration of injector actuation, during which fuel is passed through the injector from a fuel rail or like fuel supply means, is controlled by the duration of the actuation signal from the control module, that is, by the pulse width of the signal.

Reliably controlling fuel supply to an engine by controlling fuel injector actuation signal timing and duration (i.e., pulse width) assumes the absence of various possible fuel system problems, such as vapor in the fuel supply line. Thus, especially in support of maintaining the efficacy of electronic engine management devices adapted to control air/fuel ratio by controlling the actuation of fuel injectors, it would be desirable to provide an on-board diagnostic system to periodically test for the presence of fuel line vapor during engine operation. It is a primary object of the present invention to provide such on-board diagnostic system for fuel line vapor. Additional objects and features of various embodiments of the invention will be apparent from the following disclosure.

SUMMARY OF THE INVENTION

A properly running engine, having a diagnostic system as herein described, will have a characteristic fuel line pressure wave pattern for a given segment of an engine cycle, at a given point along the fuel line, under given engine operating conditions. The pressure wave pattern will include, at various frequencies and amplitudes, fuel line pressure transients resulting from fuel injector actuations, fuel pump operation, noise, etc. The on-board diagnostic system of the present invention employs analysis of fuel pressure transients in the fuel supply line of an internal combustion engine to detect the presence of vapor in the fuel line. Sensing means mounted to the fuel supply line generates a pressure signal corresponding to the transient fuel pressure waves resulting from actuation of one or more fuel injectors. The pressure signal is received by signal processing means, which optionally is incorporated into an electronic engine control module. The signal processing means analyses at least a selected frequency range of the pressure signal over a selected time interval, for example one complete engine cycle. Such analysis yields one or more values indicative of vapor volume in the fuel line, including a resonance frequency of the pressure signal. The signal processing means preferably comprises a stand-alone chip set to perform Fast Fourier Transform (FFT) analysis of the pressure signal, or comparable functionality in an EEC module. Commercially available chip sets perform FFT analysis of waveforms as a series of digital values over time. The resulting test interval resonance frequency will shift in a generally predictable manner due to the presence of vapor in the fuel supply line. The signal processing means compares the test interval resonance frequency or other indicative value to a stored value corresponding to an acceptable level of fuel line vapor. Upon detecting a difference between the test interval value and the stored value, the signal processing means generates an output signal. Optionally, it may also generate a different output signal if an unacceptable amount of vapor is not detected.

The stored resonance frequency or other value may be stored, for example, in ROM memory of an electronic engine control (EEC) module. If it corresponds to a zero vapor condition in the fuel line, the output signal indicating an unacceptable vapor level preferably is generated only when the aforesaid difference between the stored frequency and the test interval frequency exceeds a preselected differential value which also may be stored in ROM memory of an EEC module. A larger difference between the two frequencies than the stored differential value would indicate a frequency shift corresponding to an unacceptably high level of fuel line vapor. A smaller difference between the two frequencies would correspond to less fuel line vapor. Alternatively, the stored value may correspond to a preselected upper limit of vapor volume. In that case, a value difference greater than zero (in the direction of frequency shift away from the zero vapor resonance frequency) would correspond to an unacceptably high level of fuel line vapor. The stored frequency value and the stored differential value may be determined, for example, empirically or by modelling using known techniques.

In accordance with one aspect of the invention, it has been found that analysis of fuel pressure transients acquired by a single pressure transducer mounted on the engine fuel rail can reliably detect fuel line vapor. The pressure signal from the pressure transducer is processed by signal processing means preferably comprising a stand alone chip set to perform fast fourier transform (FFT) analysis of the pressure signal, or comparable functionality in an EEC module. Commercially available chip sets perform FFT analysis of waveforms as a series of digital values over time. The pressure signal is analyzed, preferably, over a selected frequency range, e.g, o to 2000 Hz, more preferably 0 to 1000 Hz, and over a test interval, e.g., a complete engine cycle, to determine the test interval resonance frequency. The test interval resonance frequency then is compared to a stored resonance frequency as discussed above. An output signal is generated in response to detection of the presence of fuel line vapor, preferably upon detection of a frequency shift corresponding to 1% by volume or greater of fuel vapor in the fuel supply line.

The output signal can actuate a warning to the operator (e.g., the driver of a vehicle) that the fuel in the vehicle is too volatile for the local environment, suggesting a change to less volatile fuel to avoid vehicle stalling due to vapor lock. This may be particularly advantageous for motor vehicles with so-called flexible fuel engines adapted to operate on any of a variety of liquid fuels. Alternatively (or in addition) the signal can actuate means for purging the fuel supply line, e.g., by increased rate of circulation of fuel in the supply line back to the fuel tank. The signal can also be used to cause an adjustment of the fuel control signals generated by the EEC module.

In accordance with one aspect of the invention, an internal combustion engine is provided with an on-board diagnostic system as described above for detecting fuel line vapor during engine operation. Fuel injector control means actuates fuel injectors to pass fuel from a fuel rail during a controlled actuation period, i.e., the time period from actuation to de-actuation of the fuel injector at the end of its fuel injection interval. Pressure sensor means provided for sensing fuel pressure in the fuel rail will generate a variable voltage signal corresponding to fuel pressure as a function of time. The pressure sensor means may employ a pressure transducer comprising, for example, a pressure responsive diaphragm exposed to the fuel in the fuel rail and a signal conditioner to generate a continuous analog voltage output pressure signal. The pressure signal from the pressure sensor means will vary over time in response to transient fuel pressure fluctuations in the fuel rail, including those resulting from fuel injector actuation. Vapor in the fuel rail will be reflected as detectable changes in the dominant resonance frequency and pressure-wave speed in the fuel line. The wave speed and/or the shift in dominant resonance frequency or other vapor-indicative value can easily be measured. The elapsed time can be measured between injector actuation (or other event of known or correlatable time) and detection of the corresponding fuel pressure fluctuations, i.e., transient fuel pressure waves at the pressure sensor means.

The present invention represents a significant advance in electronic engine control and on-board diagnosis, in part, for its recognition of the useful correspondence of such measurable changes in the transient fuel pressure waves in a fuel line, especially low-frequency pressure waves, due to the presence of vapor, and for its means and method of using such measurable changes for detecting fuel line vapor during engine operation. It should be understood that reference herein to pressure signal processing during ongoing engine operation is intended to mean not only routine on-road operation, but also test operation, e.g., immediately following initial engine or vehicle assembly. Thus, the on-board diagnosis system could be used, optionally while the engine is running without fuel ignition. In fact, a test liquid in place of gasoline or other fuel could be used, such as stoddard solvent, which like liquid fuel, gives a predictable fuel line pressure wave signal as the engine is cycled.

Additional features and advantages of the present invention will be better understood in view of the following detailed description of certain preferred embodiments.

BRIEF DESCRIPTION OF THE DRAWINGS

Certain preferred embodiments are described below with reference to the appended drawings, in which.

DETAILED DESCRIPTION OF CERTAIN PREFERRED EMBODIMENTS

While the present invention is applicable generally to any internal combustion engine burning liquid fuel supplied to fuel injectors via a fuel rail, it is particularly advantageous for four stroke multi-cylinder engines, especially motor vehicle engines. Accordingly, without intending to limit the scope of the invention, the discussion below will focus primarily on motor vehicle engines, for which on-board diagnostics of various engine performance characteristics is becoming extremely important. In that regard, reference in this discussion to a complete engine cycle is intended to mean two full revolutions of the engine. In a four stroke engine, each cylinder fires once during two full revolutions. Thus, one complete engine cycle means that each cylinder fires once.

The present invention addresses the aforesaid diagnostic need by providing an on-board diagnostic system for detecting fuel rail vapor. Certain embodiments of the on-board diagnostic system of the invention determine the vapor present in a fuel rail quantitatively, while other embodiments determine simply that vapor is present in any amount or in an amount above a selected threshold value. Upon detecting fuel line vapor, the system initiates responsive action, such as actuation of an information signal, actuation of fuel rail purging and/or actuation of remedial action by adaptive fuel injector control means to achieve desired total fuel flow with each injector actuation. As to the latter, more specifically, an output signal from the on-board diagnostic system can serve as an input signal to the engine's EEC module for adaptive air/fuel ratio control, that is, to enable the EEC computer to adjust injector actuation duration and/or timing to compensate for reduced flow rate through the injectors resulting from the fuel rail vapor. The information signal actuated by the diagnostic system may be stored for subsequent access by a service technician and/or used to cause an audible or visible warning for the vehicle operator. The fuel rail purging may involve opening a purge valve, e.g., to an auxiliary return line to the fuel tank or to a vapor treatment device. Since fuel injection systems typically circulate fuel continuously through the fuel rail and back to the fuel tank in their ordinary operating mode purging may also be accomplished in some system by accelerating fuel flow through the fuel rail, as by increasing the rate of fuel pumping from the fuel tank.

Figure 1A:
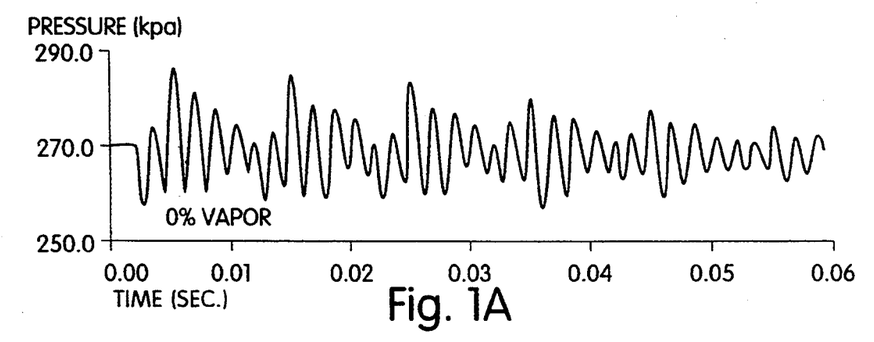
FIGS. 1A through 1D are graphs illustrating the effect of various different levels of vapor in the fuel rail of an engine having six cylinders and six corresponding fuel injectors, on the transient fuel pressure waves at a pressure transducer mounted on the fuel rail, with the engine operating at 2000 rpm and each injector being actuated in turn for 2.5 milliseconds within each ten millisecond interval.
Figure 1B:
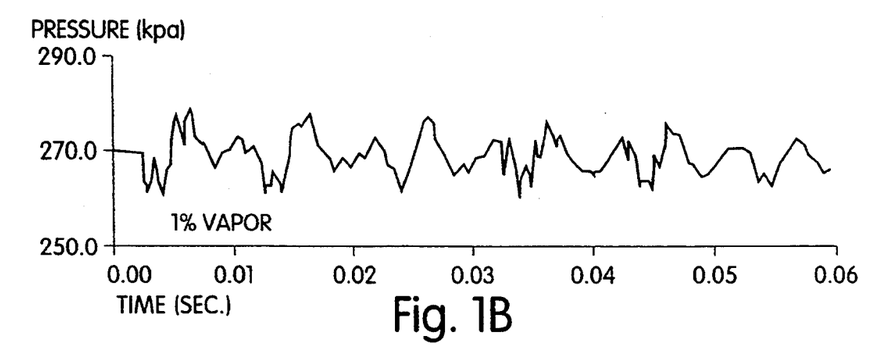
Figure 1C:
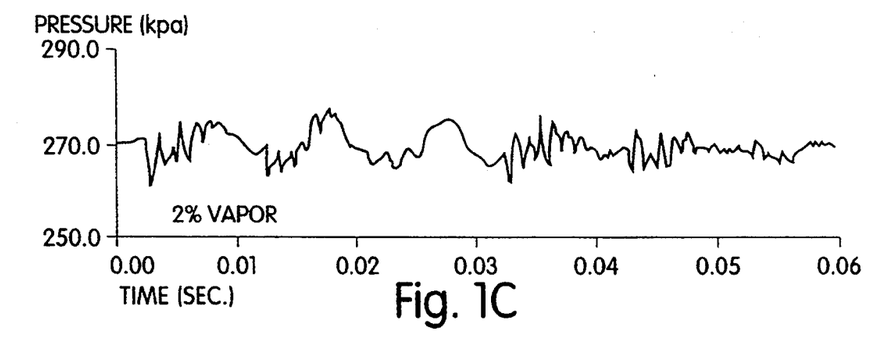
Figure 1D:
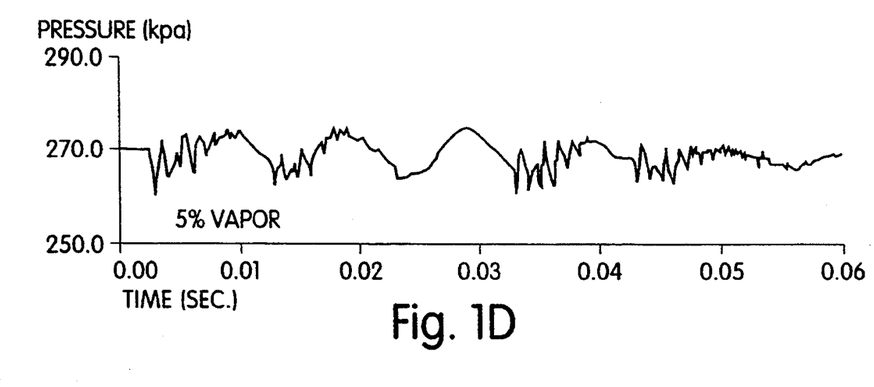

The graphs in FIGS. 1A through 1D show fuel pressure transients at a pressure transducer sensing fuel rail pressure. More specifically, the graphs plot fuel line pressure as a function of time. FIG. 1A shows fuel pressure transients for a system having essentially no fuel line vapor. FIG. 1B shows the pressure transients when there is about 1% by volume vapor in the fuel line. The vapor "softens" the system (comprising the fuel, fuel rail, etc.), changing its wave pattern or signature. FIGS. 1C and 1D show the further changes when vapor is increased to 2% and 5% by volume, respectively. The values shown in the graphs of FIGS. 1A through 1D were generated by a computer model in accordance with known algorithms and techniques and are quite close to actual test results. Thus, comparable pulse waveforms are obtained using a pressure transducer having a variable voltage output signal proportional to pressure within the fuel rail, with zero volts preferably corresponding to substantially static equilibrium pressure within the fuel rail (established by a pressure regulator) without fuel injector actuation. Given an actuation commencing at time 0.00 seconds on the graph, pressure in the fuel rail is seen to drop at the location of the pressure transducer in response to such actuation after a wave propagation delay period. The output voltage of the pressure transducer would drop correspondingly. Pressure recovers after the actuation interval, that is, after the fuel injector is closed. It can be seen in FIGS. 1A through 1D that the pulse waveform resulting from actuation of a fuel injector changes with increasing fuel line vapor. The change in pulse waveforms has been found to correlate quite well with the quantitative difference in fuel line vapor.

Figure 2A:
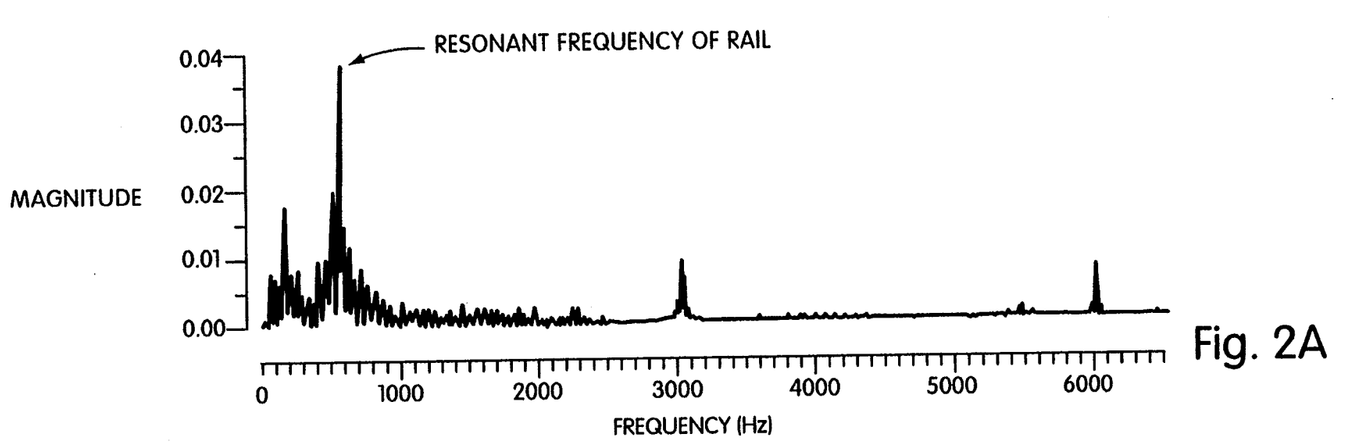
FIGS. 2A and 2B illustrate the shift in resonance frequency due to vapor in a fuel rail of such engine.
Figure 2B:
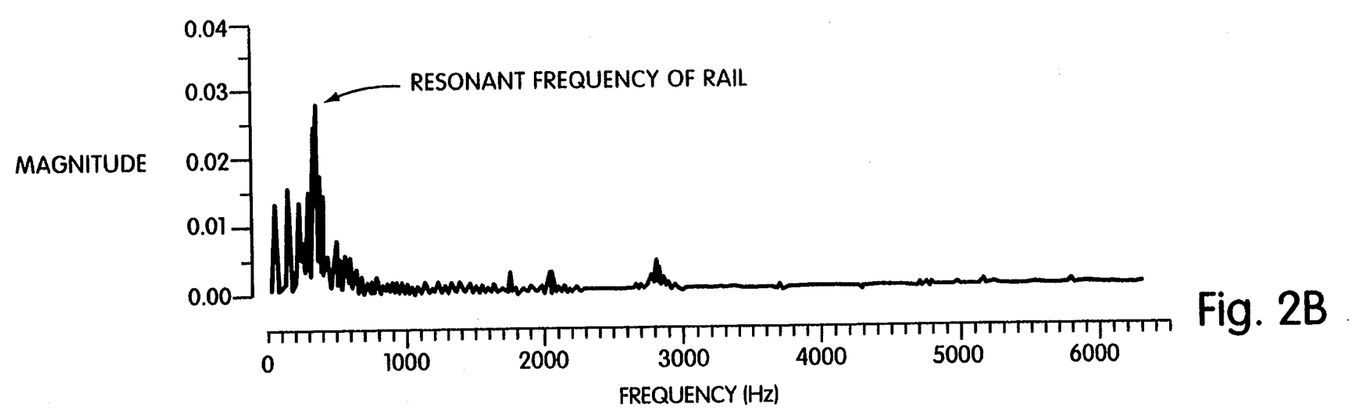

In particular, referring now to FIGS. 2A and 2B, the change in pressure signal due to fuel engine vapor is shown as a shift in resonance frequency. Vapor in the fuel line "softens" the system, resulting in a lower resonance frequency. FIG. 2A shows the frequency spectrum developed by FFT analysis of the pressure signals received by the signal processor for a test interval of one complete engine cycle. The signal processor can select test intervals based on signals from the engine's EEC module or other fuel control means. Optionally, to enhance accuracy or reliability, the FFT frequency spectrum can be combined, e.g., by averaging, with that of one or more additional such single cycle test intervals. In this way, the possibility is reduced of a false indication of fuel line vapor due to aberrant fuel pressure transients during a test interval. Similarly, the output signal may be generated only when two or more test intervals in a preselected number of consecutive test signals each separately indicates an unacceptable level of fuel line vapor. Thus, for example, the output signal may be generated by the signal processor only when at least three of the last five, or ten of the last fifteen or twenty test intervals indicates vapor. Preferably, the test interval results would be stored in RAM memory, with the result for each new test interval replacing the oldest stored result (i.e., first-in first-out).

As stated above, the frequency graph in FIG. 2A, corresponding to no fuel line vapor, shows a maximum peak at about 550 Hz. The peak at 550 Hz identifies the natural, 1st resonance frequency of the system. In contrast, the graph of FIG. 2B, corresponding to fuel line vapor of about 1% by volume, has a resonance frequency of about 350 Hz. The 200 Hz value difference between the two resonance frequencies is the frequency shift resulting from fuel line vapor. FIG. 2B also reveals that the magnitude of the resonance frequency is reduced. Determination of fuel line vapor may also be based on such reduction in magnitude and/or on the corresponding increase in magnitude of frequency peaks at the low frequency end of the spectrum. In preferred embodiments, the value difference above which an output signal is generated by the signal processing means preferably corresponds to volume in the fuel line of 1% or greater by volume, typically a shift of 200 Hz or greater. As discussed above, such value can be stored for comparison to the actual value difference found for a given test interval.

Since the shift in dominant resonance frequency varies directly with the volume percentage of vapor in the fuel rail, it can be used by the signal processing means to determine either the simple presence of vapor (above a threshold volume of zero or more) or a quantitative value corresponding to the volume percentage of vapor in the fuel rail. The correspondence between vapor volume and frequency shift, for a series of vapor volume percentages can be determined for a given engine either empirically or by modelling, etc. Optionally, such corresponding values can be stored in memory (e.g., in ROM memory of the EEC) as a look-up table accessible by the signal processing means. The output signal of the signal processing means may indicate the amount of vapor in the fuel line or simply that vapor is present. The latter is sufficient if the output signal is used only to actuate a warning device to alert the operator, e.g., a vehicle driver, of the presence of vapor. The signal may in that case be generated by the signal processing means when its processing of the pressure transducer signal indicates the presence of vapor in an amount above zero volume percent or other amount selected empirically, by modelling, etc.

In certain embodiments of the invention, the on-board diagnostic system is integrated with adaptive air/fuel control means. In accordance with such embodiments the air/fuel control means can employ the output signal from the signal processing means indicating the presence of vapor or, optionally, indicating the amount of vapor present, as an input value in calculating injector actuation signal timing and/or duration.

To synchronize acquisition of pressure waveforms with the actuation of injectors, analyzer triggering (i.e., the point where time=0 for each plotted waveform) preferably is set to a fixed current shunt voltage (+80 mv) of a selected injector at the injector controller. The delay of pressure response relative to the trigger event (i.e., the propagation delay) for the transient waveform can be used to estimate the travel time of the pressure disturbances from the injector nozzle to the pressure transducer. However, the exact propagation delay need not be precisely known. The time interval over which the pressure signal is analyzed should be sufficiently large to cover the arrival of the fuel pressure transients at the pressure transducer either with or without slowing due to fuel line vapor, etc.

Figure 3:
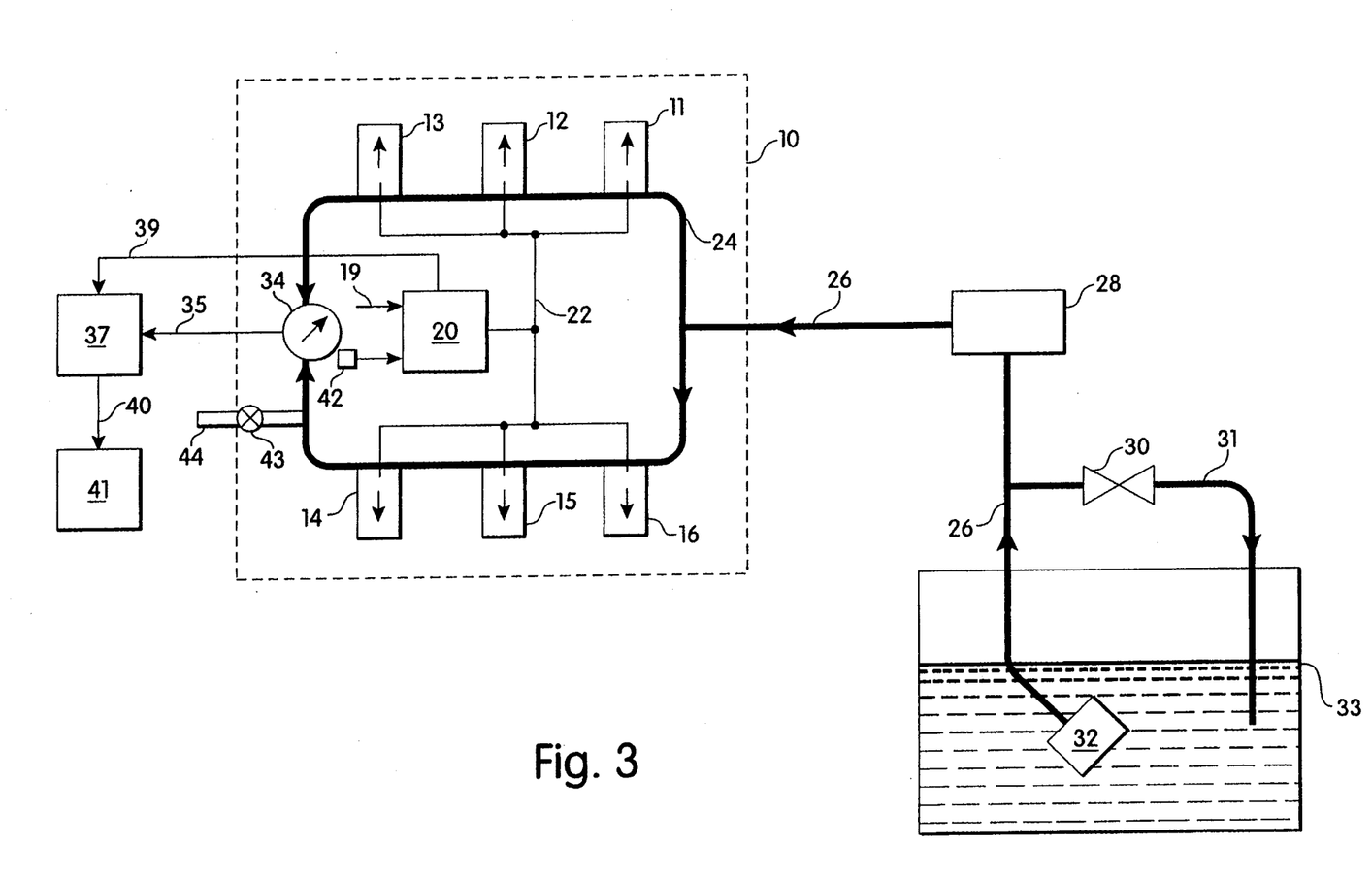
FIG. 3 is a schematic illustration of an internal combustion engine fuel system comprising an on-board diagnostic system for detecting fuel rail vapor during engine operation in accordance with a first embodiment of the invention.

A preferred embodiment of the invention is illustrated in FIG. 3, wherein a six cylinder engine 10 is seen to comprise a fuel supply system for supplying gasoline under pressure to the combustion cylinders of the engine. The fuel supply system consists of high pressure electric Gerotor-type pump 32 delivering fuel from a storage tank 33 through an inline fuel filter 28 to a fuel charging manifold assembly 24 via solid and flexible fuel lines. The fuel charging manifold assembly, referred to as a fuel rail, supplies fuel to electronically actuated fuel injectors 11-16 mounted on an air intake manifold directly above each of the engine's intake valves. Air entering the engine is measured by a mass airflow meter. Air flow information and input from other engine sensors 19 is used by an onboard engine electronic control computer 20 to calculate the required fuel flow rate necessary to maintain a prescribed air/fuel ratio for a given engine operation. The injectors, when energized, spray a predetermined quantity of fuel in accordance with engine demand. The duration of the actuation period during which the injectors are energized, determined by the actuation signal pulse width, is controlled by the vehicle's EEC computer 20. Thus, the EEC computer serves as the fuel injector control means, and, typically, performs various additional engine control functions.

The fuel injector is an electromechanical device that atomizes the fuel delivered to the engine. Injectors typically are positioned so that their tips direct fuel at the engine intake valves. The valve body consists of a solenoid actuated pintle or needle valve assembly that sits on a fixed size orifice. A constant pressure drop is maintained across the injector nozzles via a pressure regulator. An electrical signal from the EEC unit activates the solenoid, causing the pintle to move inward, off the seat, allowing fuel to flow through the orifice.

In the embodiment of FIG. 3, fuel injector control means 20 has injector signal output means 22 connected to the injector drivers of the fuel injectors 11-16. Injector signals from fuel injector control means 20 control the sequence and timing of fuel injector actuation, including the duration of the actuation period during which each fuel injector, in turn, is open to pass fuel from fuel rail 24 to the respective combustion chamber. A pressure regulator 30 is provided for regulating fuel pressure in fuel rail 24. Pressure regulator 30 is located proximate to fuel pump 32. That is, it is closer to fuel pump 32 than to the fuel rail 24 and is upstream of the fuel filter 28. Locating the pressure regulator 30 proximate to the fuel pump is found to provide enhanced accuracy of pressure readings by pressure sensor means 34 mounted on fuel rail 24. Suitable regulators are commercially available and will be apparent to those skilled in the art in view of the present disclosure. The fuel pressure regulator typically is a diaphragm operated relief valve with one side of the diaphragm sensing fuel pressure and the other side subjected to intake manifold pressure. The nominal fuel pressure is established by a spring preload applied to the diaphragm. Referencing one side of the diaphragm to manifold pressure aids in maintaining a constant pressure drop across the injectors. Fuel in excess of that used by the engine passes through the regulator and returns to the fuel tank 33 via shunt line 31.

Suitable pressure sensor means are commercially available and include, for example, variable reluctance, differential pressure transducers. Preferably the transducer has good transient response to low frequency transient pressure waves, low frequency here meaning 1 KHz or lower. The pressure sensor means preferably also has a high output signal with low susceptibility to electrical noise and good durability to withstand vibrations and shock experienced in a motor vehicle engine environment. Employing pressure sensor means having a transducer diaphragm vented on one side to atmosphere allows gage measurement of pressure (PSIG). The output signal from the pressure transducer preferably is a continuous analog voltage out signal, where signal voltage varies directly with fuel pressure. Zero voltage can be set to the nominal fuel pressure established for the fuel rail. The pressure signal from the pressure sensor means 34 may further comprise signal conditioning means. Thus, the pressure transducer may be connected by a shielded cable to a signal conditioner. Suitable signal conditioners for various suitable pressure transducers are commercially available and will be apparent to those skilled in the art in view of the present disclosure. In accordance with such preferred embodiment, the transducer signal conditioner sources the pressure transducer with excitation power and amplifies the transducer output. The resulting pressure signal, that is, analog voltage output 35 of the pressure sensor means 34 is, therefore, proportional to fuel rail pressure sensed by the pressure transducer.

The pressure signal is input to signal processing means 37 for generating an output signal in response thereto. Signal processing means 37 can be, for example, a programmable waveform analyzer, various models of which are commercially available and will be readily apparent to those skilled in the art in view of this disclosure. Such analyzers digitize and store analog voltage signals. The signal processing means preferably is responsive to a timing signal 39 from the fuel injector control means 20 to synchronize acquisition of pressure waveforms with the actuation of the individual injectors. The delay between the sending of the actuation signal and the arrival at the pressure sensor means of the resulting transient fuel pressure waveform is readily obtained empirically for any given application of the invention (i.e., for any given engine arrangement). Those skilled in the art will recognize that such propagation delay will vary from injector to injector, depending on such factors as the distance along a fuel rail between the pressure sensor means and the individual injector. The test interval should be sufficiently large to cover the arrival time of the pressure transient even if its travel from the injector to the pressure sensor is slowed by vapor in the fuel rail.

Typically, the signal processing means will employ a test interval equal in length to a single full engine cycle, with signal value acquisitions every 100 to 500 microseconds ($\mu s$). Thus, at an engine operating speed of 1000 RPM, for a six cylinder engine, the test interval would be 120 ms, with 240 to 1200 pressure signal value acquisitions to be processed. Those who are skilled in this technology will recognize that frequent sampling will yield more accurate or reliable results when processed, e.g., to produce a frequency spectrum by Fast Fourier Transform analysis as discussed above.

Output signal 40 from signal processing means 37 is received by utilization means 41. As discussed above, utilization means 41 may comprise, for example, an indicator light and/or means for operating purge means, such as purge valve 43 to pass vapor from fuel rail 24 to fuel tank 33 or other vapor receiving means via conduit 44.

The fuel injector control means 20 optionally comprises memory means 42, for example, a look-up table, from which it may obtain an adjustment value for fuel injection control based on the value of the output signal 40 from the signal processing means 37. In that case, utilization means 41 may comprise functionality within fuel injector control means 20.

Figure 4:
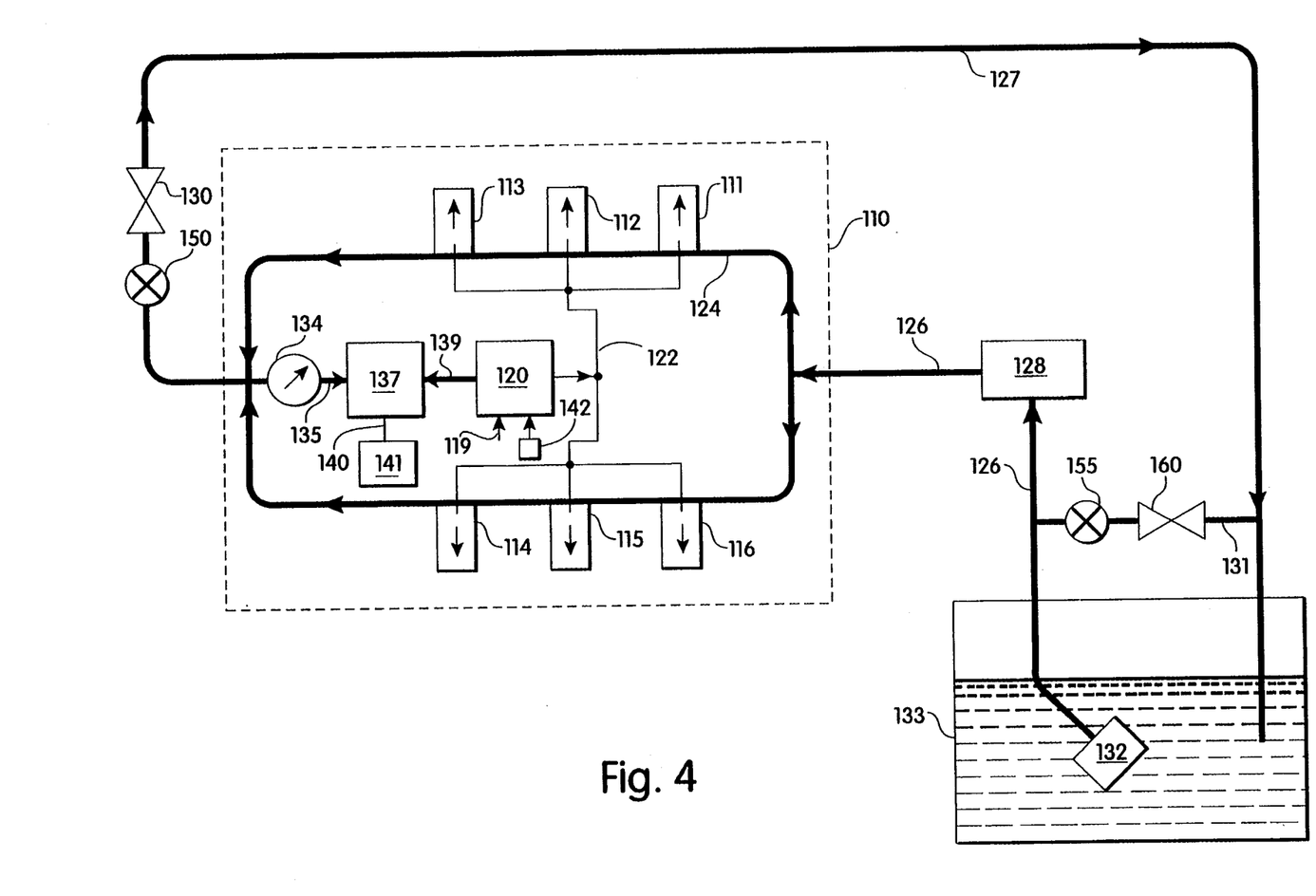
FIG. 4 is a schematic illustration of an internal combustion engine fuel system having an on-board diagnostic system for detecting fuel rail vapor in accordance with a second embodiment of the invention.

A second preferred embodiment of the invention is schematically illustrated in FIG. 4. The embodiment of FIG. 4 involves a more traditional fuel injection supply line, in that a fuel return line is provided downstream of the fuel rail. The system is modified, however, to deadhead the system during vapor testing, as now described. In addition, the pressure regulator is relocated to a location proximate the fuel pump, as in the embodiment of FIG. 3. Locating the regulator remote from the fuel rail can provide individual injector transients in the aggregate waveform having more uniform pulse-to-pulse amplitudes and signatures. Fuel pump 132 is mounted in fuel tank 133 in the customary manner. Fuel is supplied during normal engine operation via supply line 126 which passes through fuel filter 128 to fuel rail 124. Fuel rail 124 feeds fuel to 6 fuel injectors 111 through 116 which are actuated by actuation signals 122 from fuel injector control means 120. As in the embodiment of FIG. 3, fuel injector control means 120 preferably is incorporated into an electronic engine control module or computer which performs various additional engine control functions.

Engine 110 in the embodiment of FIG. 4 is adapted for normal engine operation, during which fuel line vapor is not analyzed. Engine 110 also is adapted for fuel line vapor testing operation during ongoing engine operation. During fuel line vapor testing, the fuel supply line is altered by appropriate valving, including first valve means 150 in the fuel return line 127 for deadheading the fuel rail. Specifically, during testing valve means 150 closes the fuel return line to fuel flow from the fuel rail. During normal engine operation valve means 150 opens the fuel return line 127 to fuel flow from the fuel rail 124. Second valve means 155 is provided in fuel shunt line 131 for closing the fuel shunt line during normal engine operation and for opening the fuel shunt line during vapor testing. During normal engine operation, with first valve means 150 open and second valve means 155 closed, pressure in the fuel rail is regulated by pressure regulator 130 in fuel return line 127. During testing operation, with first valve means 150 closed to deadhead the fuel rail and second valve means 155 open, pressure is regulated by pressure regulator 160 in shunt line 131.

Fuel line vapor diagnosis in the embodiment of FIG. 4 is carried out substantially in accordance with the various techniques discussed above. Thus, timing signal 139 is sent by fuel injector control means 120 to signal processing means 137 to trigger measurement of a propagation delay period after which the signal processing means 137 conducts signal sampling of signal 135 from pressure sensor 134.

Those skilled in the art will recognize that the subject matter disclosed herein can be modified and/or implemented in alternative embodiments without departing from the true scope and spirit of the present invention as defined by the following claims.

We claim:

1. An on-board diagnostic system for determining the presence of vapor in a fuel supply line of an internal combustion engine during engine operation, the engine having at least one fuel injector operatively connected to the fuel supply line, the diagnostic system comprising:

sensing means operatively mounted to the fuel supply line for sensing transient fuel pressure wave in the fuel supply line resulting from actuation of the fuel injector, and for generating a pressure signal corresponding to the transient fuel pressure waves at least over a selected frequency range;

signal processing means operatively connected to the sensing means for receiving and processing the pressure signal for detecting the presence of vapor in the fuel supply line by determining a resonance frequency of the transient fuel pressure waves, at least over a selected test interval, and comparing the test interval resonance frequency to a stored resonance frequency corresponding to an acceptable vapor level in the fuel supply line, and for generating an output signal upon detecting a value difference between the test interval resonance frequency and the stored resonance frequency; and utilization means operatively connected to the signal processing means for receiving the output signal and manifesting its presence.

2. The on-board diagnostic system of claim 1 wherein the internal combustion engine is a multi-cylinder four stroke engine, and wherein the fuel supply line comprises a fuel rail to which multiple said fuel injectors are operatively connected, and wherein the test interval consists of at least one complete engine cycle.

3. The on-board diagnostic system of claim 2 wherein the sensing means comprises a pressure transducer having a pressure responsive diaphragm exposed to fuel in the fuel rail and a signal conditioner to generate said pressure signal as a continuous analog voltage output signal.

4. The on-board diagnostic system of claim 1 wherein the value difference between the test interval resonance frequency and the stored resonance frequency corresponds to at least 1% vapor volume in the fuel supply line.

5. The on-board diagnostic system of claim 1 wherein the value difference between the test interval resonance frequency and the stored resonance frequency is at least 200 Hz or higher.

6. The on-board diagnostic system of claim 1 wherein the utilization means comprises an indicator light which illuminates in response to the output signal.

7. The on-board diagnostic system of claim 1 wherein the utilization means comprises a purge means for venting vapor from the fuel supply line in response to the output signal.

8. The on-board diagnostic system of claim 7 wherein the purge means comprises a purge valve which opens in response to the output signal to establish fluid communication between the fuel supply line and means for receiving vapor from the fuel supply line.

9. An on-board diagnostic system for determining the presence of vapor in a fuel supply line of an internal combustion engine during engine operation, the engine having at least one fuel injector operatively connected to the fuel supply line, the diagnostic system comprising:

sensing means operatively mounted to the fuel supply line for sensing transient fuel pressure waves in the fuel supply line resulting from actuation of the fuel injector, and for generating a pressure signal corresponding to the transient fuel pressure waves at least over a selected frequency range;

signal processing means comprising a fast fourier transform analyzer operatively connected to the sensing means for receiving and processing the pressure signal for detecting the presence of vapor in the fuel supply line by determining a resonance frequency of the transient fuel pressure waves, at least over a selected test interval, and comparing the test interval resonance frequency to a stored resonance frequency corresponding to an acceptable vapor level in the fuel supply line, and for generating an output signal upon detecting a value difference between the test interval resonance frequency and the stored resonance frequency; and utilization means operatively connected to the signal processing means for receiving the output signal and manifesting its presence.

10. A multi-cylinder four stroke internal combustion engine having a fuel rail for supplying fuel to multiple fuel injectors operatively connected to the fuel rail, and having an on-board diagnostic system for detecting vapor in the fuel rail during engine operation, said diagnostic system comprising:

a pressure transducer having a pressure responsive diaphragm exposed to fuel in the fuel rail and a signal conditioner to generate a continuous analog voltage output pressure signal corresponding to transient fuel pressure waves at least over the frequency range of 0 to 1000 Hz;

signal processing means for receiving the pressure signal of the pressure transducer, determining a dominant resonance frequency thereof by fast fourier transform analysis over a test interval of at least one complete engine cycle, comparing the test interval dominant resonance frequency to a stored resonance frequency corresponding to an acceptable fuel line vapor level of between one and five volume percent vapor, and generating an output signal upon detecting at least a preselected value difference between the test interval resonance frequency and the stored resonance frequency; and utilization means for receiving the output signal from the signal processing means and for manifesting its presence at least by illuminating an indicator light in response thereto.

11. The multi-cylinder four-strike internal combustion engine of claim 10 wherein the fuel rail is deadheaded at least during said test interval.

* * * * *